United States Patent [19]

Takahashi et al.

[11] Patent Number: 5,138,059
[45] Date of Patent: Aug. 11, 1992

[54] DC-89 COMPOUNDS AND PROCESS FOR THEIR PREPARATION

[75] Inventors: Keiichi Takahashi, Susono; Michio Ichimura, Shizuoka; Shigeo Katsumata, Mishima; Tatsuhiro Ogawa; Makoto Morimoto, both of Shizuoka; Tadashi Ashizawa, Numazu; Masaji Kasai, Fujisawa; Kenichi Muroi, Hofu; Hiromitsu Saito, Sagamihara; Hiroshi Sano, Machida; Toru Yasuzawa, Sakai, all of Japan

[73] Assignee: Kyowa Hakko Kogyo Co., Ltd., Tokyo, Japan

[21] Appl. No.: 380,379

[22] Filed: Jul. 17, 1989

[30] Foreign Application Priority Data

Jul. 22, 1988 [JP] Japan .................. 63-182866
Oct. 21, 1988 [JP] Japan .................. 63-265580

[51] Int. Cl.$^5$ .............. C07D 487/04; C07D 471/06
[52] U.S. Cl. ............................ 546/84; 548/433
[58] Field of Search ................. 548/433; 546/84

[56] References Cited

U.S. PATENT DOCUMENTS

| | | | |
|---|---|---|---|
| 4,169,888 | 10/1979 | Hanka et al. | 435/886 |
| 4,400,518 | 8/1983 | Wierenga | 548/433 |
| 4,413,132 | 11/1983 | Wierenga | 548/491 |
| 4,423,228 | 12/1983 | Wierenga | 548/421 |
| 4,423,229 | 12/1983 | Wierenga | 548/421 |
| 4,423,230 | 12/1983 | Wierenga | 548/433 |
| 4,994,578 | 2/1991 | Ohba et al. | 546/84 |

FOREIGN PATENT DOCUMENTS

| | | |
|---|---|---|
| 0154445 | 2/1985 | European Pat. Off. |
| 8706265 | 10/1987 | European Pat. Off. |
| 0271581 | 6/1988 | European Pat. Off. |
| 8804659 | 6/1988 | European Pat. Off. |
| 0318056 | 5/1989 | European Pat. Off. |
| 0339681 | 11/1989 | European Pat. Off. |

OTHER PUBLICATIONS

Warpehoski et al., J. Med. Chem., vol. 31, (1988), pp. 590-603.
Wierenga et al., Adv. Enzyme Regul., Antitumor Analogs of CC-1065, pp. 143-155.
L. Yasuzawa et al., Chem. Pharm. Bull., vol. 36(9), pp. 3728-3731 (1988).

Primary Examiner—Mary E. Ceperley
Attorney, Agent, or Firm—Fitzpatrick, Cella, Harper & Scinto

[57] ABSTRACT

Novel DC-89 compounds represented by the general formula:

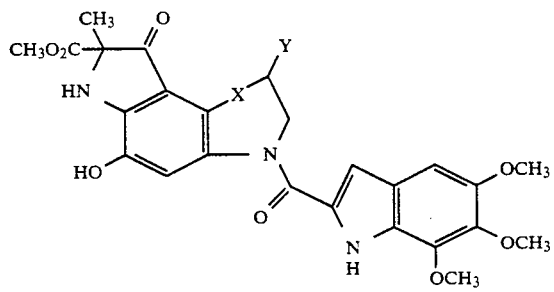

wherein X represents a single bond or $-CH_2-$; and when X represents a single bond, Y represents $-CH_2Br$ or $-CH_2Cl$ and when X represents $-CH_2-$, Y represents Br, are obtained by the present invention. The compounds have antibacterial and anti-tumor activity.

1 Claim, 6 Drawing Sheets

DC-89 COMPOUNDS AND PROCESS FOR THEIR PREPARATION

BACKGROUND OF THE INVENTION

The present invention relates to novel compounds DC-89A2, DC-89B1 and DC-89B2, which are generically referred to as DC-89 compounds hereinafter, and to processes for preparing the DC-89 compounds and a known compound DC-89A1. The DC-89 compounds of the present invention have antibacterial and anti-tumor activity and are useful as antibacterial and anti-tumor agents.

As the low-molecular substances having antibacterial and anti-tumor activity and obtained from microorganisms or plants, many compounds such as anthracycline compounds, anthraquinone compounds and mitomycin compounds have so far been reported (CRC Handbook of Antibiotic Compounds, CRC Press, U.S.A., 1981).

Further, as the compounds analogous to the DC-89 compounds, DC-88A and DC-89A1 which have antibacterial and anti-tumor activity and which are produced by microorganisms belonging to the genus Streptomyces are disclosed in WO 87/06265 (EP-A-0271581).

SUMMARY OF THE INVENTION

Excellent antibiotics and anti-tumor compounds are always in demand.

The present inventors have acquired many microorganisms from nature and have examined them for productivity of antibiotics. As a result, it has been found that antibiotics which are different from DC-88A and DC-89A1 and which possess anti-tumor activity are produced in the culture of the DC-88A and DC-89A1-producing microorganism belonging to the genus Streptomyces. Isolation and purification of the antibiotics has revealed that they are novel compounds, and they have been named DC-89A2, DC-89B1, and DC-89B2, respectively. The structural formula of DC-89A2, DC-89B1, DC-89B2 and DC-89A1 is shown below.

DC-89A1: X = —CH$_2$—, Y = Cl
DC-89A2: X = single bond, Y = —CH$_2$Cl
DC-89B1: X = —CH$_2$—, Y = Br
DC-89B2: X = single bond, Y = —CH$_2$Br

DETAILED DESCRIPTION OF THE INVENTION

The physicochemical properties of DC-89A2, DC-89B1 and DC-89B2 are shown below.

DC-89A2

Figure 1:
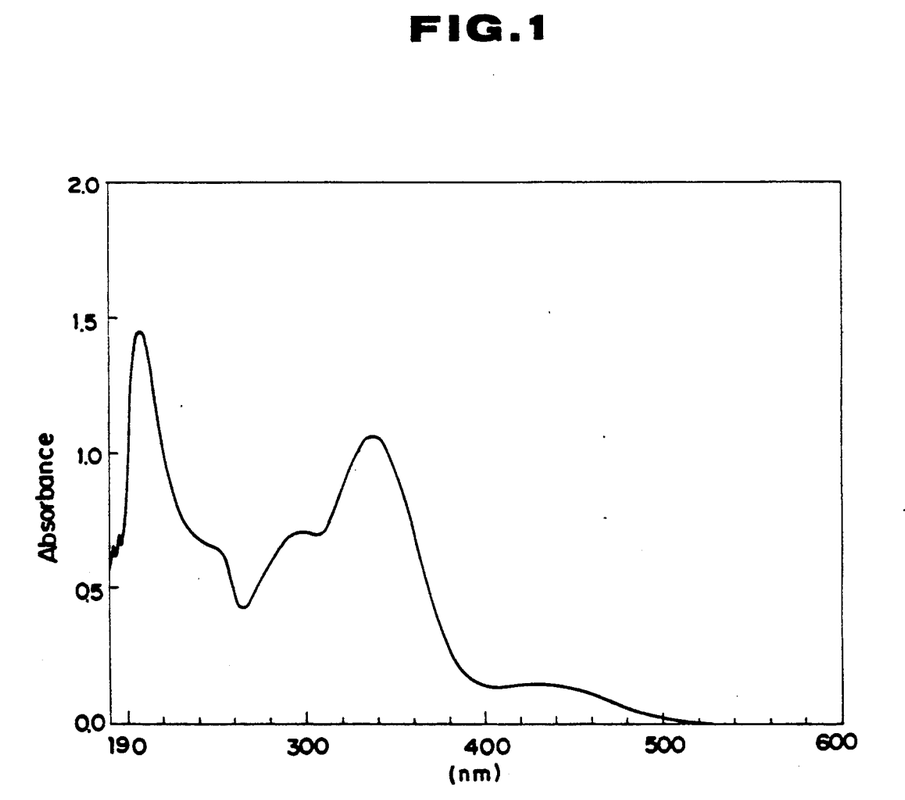
FIG. 1 shows the UV absorption spectrum of DC-89A2 in methanol solution.
Figure 2:
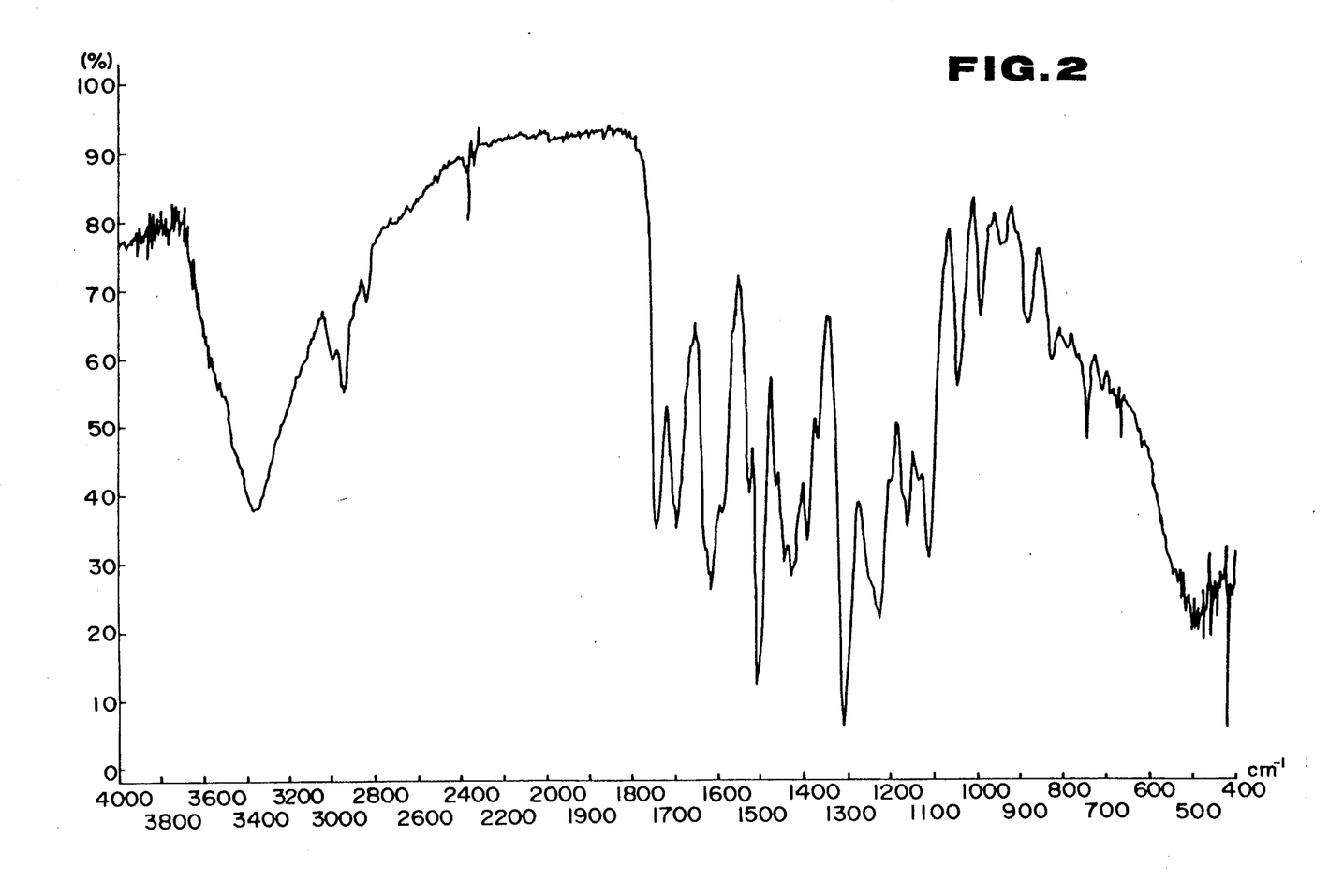
FIG. 2 shows the IR absorption spectrum of DC-89A2 (KBr tablet).

(1) Elemental analysis: C 57.2%, H 4.9%, N 7.8%
(2) Molecular formula: $C_{26}H_{26}ClN_3O_8$
(3) Molecular weight: 543 (mass spectrum)
(4) Melting point: 238°–240° C. (decomposed)
(5) Ultraviolet absorption spectrum (in methanol): As shown in FIG. 1
(6) Infrared absorption spectrum (KBr tablet): As shown in FIG. 2
(7) Specific rotation: $[\alpha]_D^{20} = -140.5°$ (CH$_3$OH solution)
(8) PMR spectrum (in CDCl$_3$, internal standard TMS) 9.59(1H,s), 8.51(1H,s), 6.98(1H,d), 6.83 (1H,s), 4.56(2H,broad dd), 4.13(1H,m), 4.11(3H,s), 3.95(3H,s), 3.91(3H,s), 3.72 (3H,s), 3.70(2H,broad dd), 1.70(3H,s)
(9) CMR spectrum (in CDCl$_3$, internal standard TMS) 196.6, 169.6, 160.5, 150.4, 150.1, 144.2, 140.9, 138.7, 137.7, 129.1, 126.0, 123.5, 119.5, 115.6, 112.5, 107.9, 98.0, 71.2, 61.5, 61.2, 56.4, 55.0, 53.4, 46.4, 42.3, 22.0
(10) Solubility: readily soluble in methanol, ethanol, ethyl acetate, acetone, chloroform and dimethylsulfoxide; sparingly soluble in water and n-hexane.

DC-89B1

Figure 3:
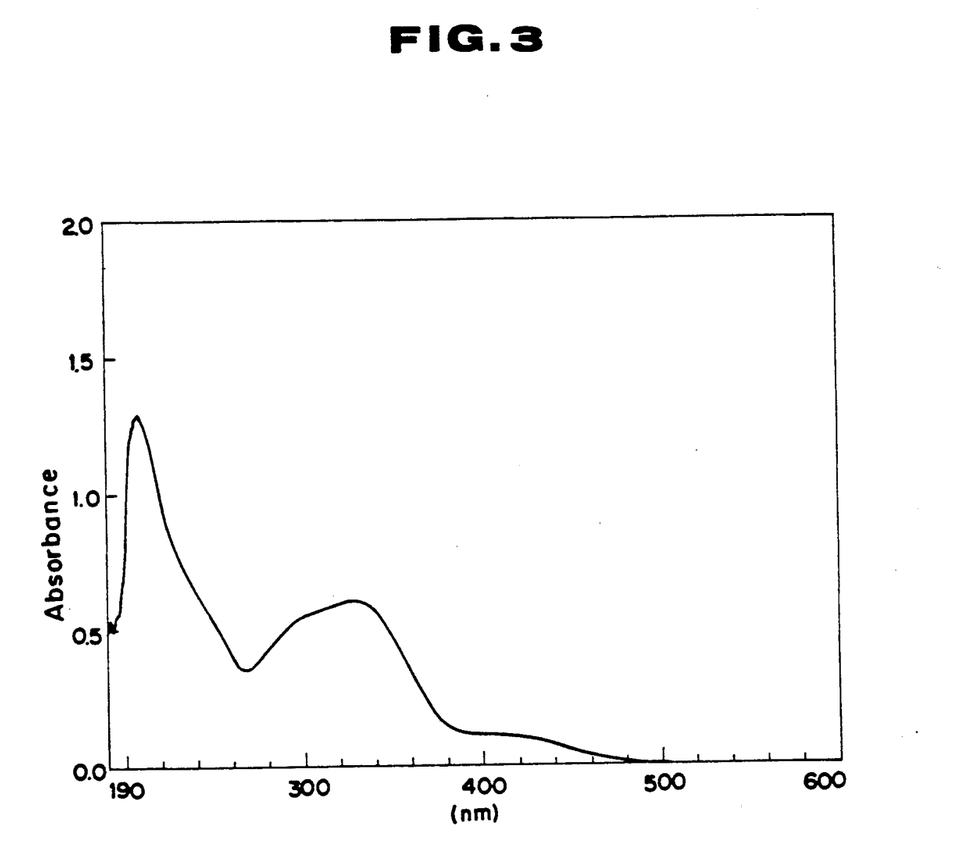
FIG. 3 shows the UV absorption spectrum of DC-89B1 in methanol solution.
Figure 4:
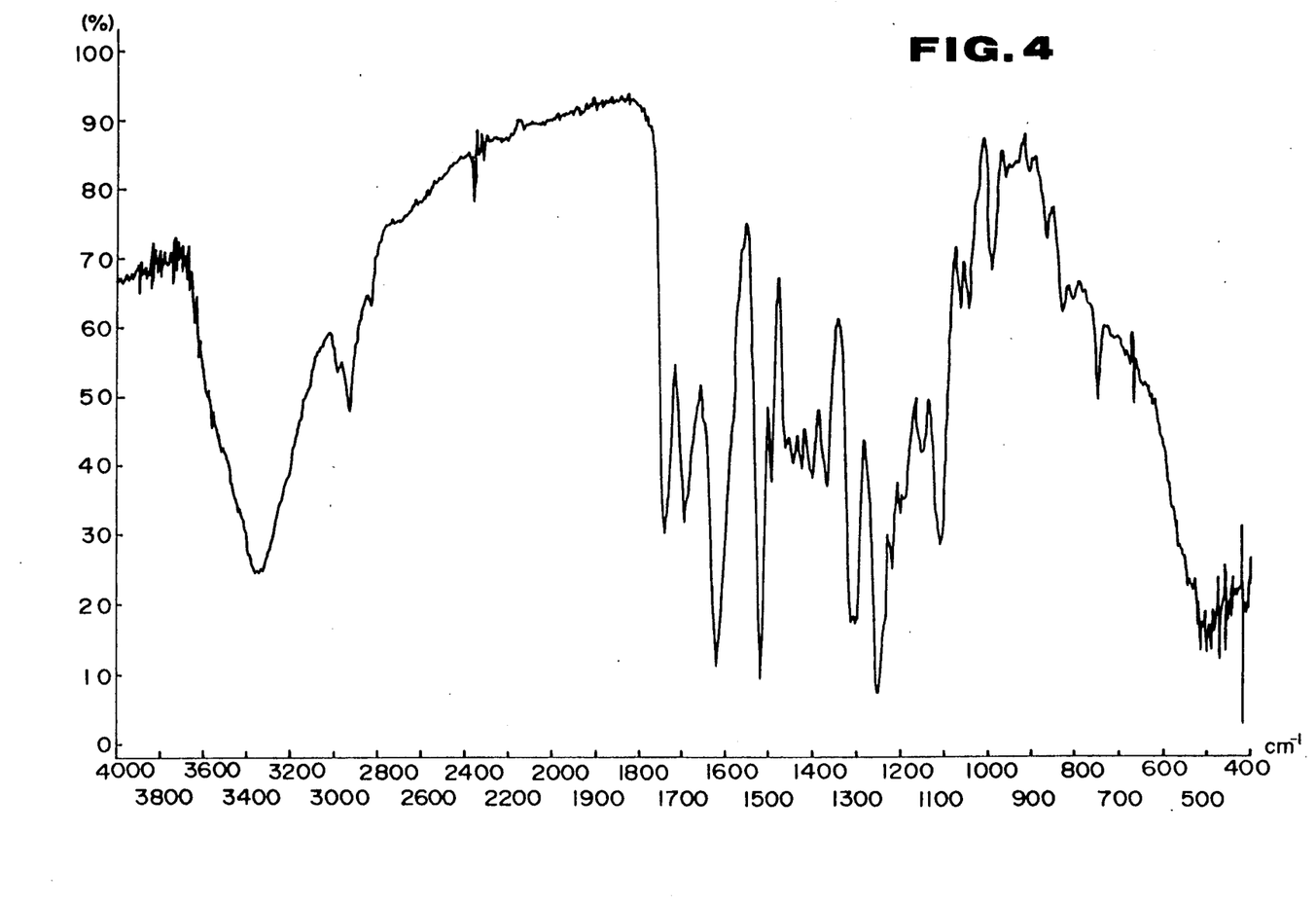
FIG. 4 shows the IR absorption spectrum of DC-89B1 (KBr tablet).

(1) Elemental analysis: C 53.4%, H 4.7%, N 6.5%
(2) Molecular formula: $C_{26}H_{26}BrN_3O_8$
(3) Molecular weight: 588 (mass spectrum)
(4) Melting point: 148°–149° C.
(5) Ultraviolet absorption spectrum (in methanol): As shown in FIG. 3
(6) Infrared absorption spectrum (KBr tablet): As shown in FIG. 4
(7) Specific rotation: $[\alpha]_D^{20} = -113.5°$ (CH$_3$OH solution)
(8) PMR spectrum (in CDCl$_3$, internal standard TMS) 9.37(1H,s), 8.06(1H,s), 7.09(1H,s), 6.71 (1H,s), 6.62(1H,d), 4.58(1H,dd), 4.55 (1H,m), 4.09(1H,d), 3.99(3H,s), 3.89(3H,s), 3.81(3H,s), 3.75(1H,dd), 3.74(3H,s), 3.63 (1H,dd), 1.64(3H,s)
(9) CMR spectrum (in CDCl$_3$, internal standard TMS) 196.8, 169.7, 164.5, 151.7, 150.2, 141.6, 140.4, 138.9, 129.1, 128.9, 126.1, 123.1, 117.1, 116.6, 118.2, 108.3, 97.9, 71.1, 61.5, 61.2, 56.3, 53.4, 53.0, 44.8, 33.9, 21.8
(10) Solubility: readily soluble in methanol, ethanol, ethyl acetate, acetone, chloroform and dimethylsulfoxide; sparingly soluble in water and n-hexane.

DC-89B2

(1) Elemental analysis: C 53.2%, H 4.5%, N 7.2%
(2) Molecular formula: $C_{26}H_{26}BrN_3O_8$
(3) Molecular weight: 588 (mass spectrum)
(4) Melting point: 214°–215° C. (decomposed)

Figure 5:
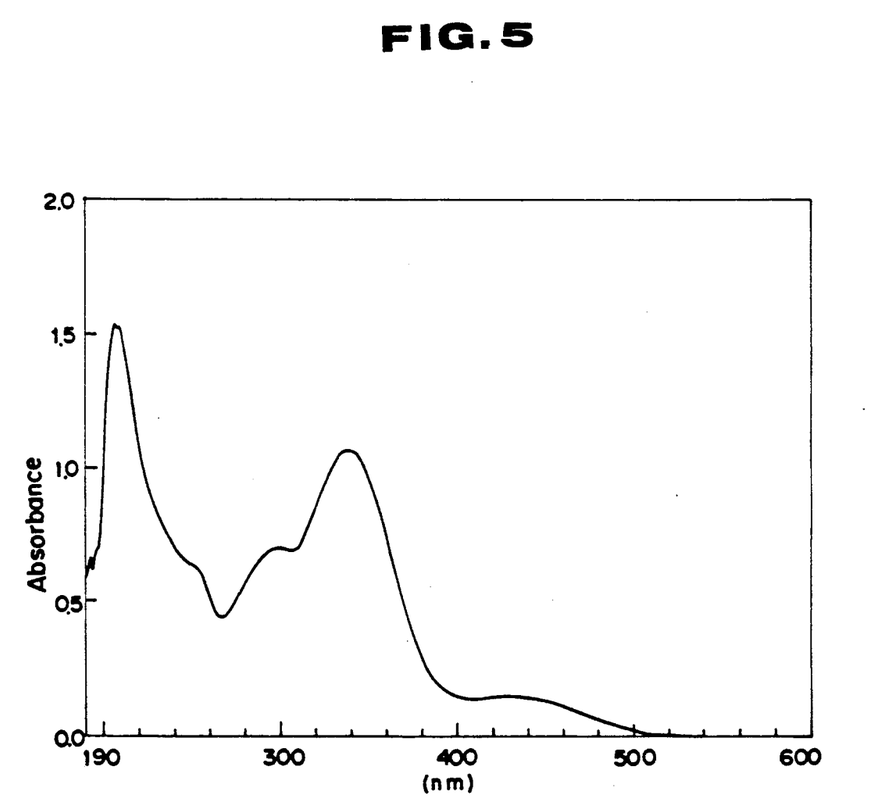
FIG. 5 shows the UV absorption spectrum of DC-89B2 in methanol solution.

(5) Ultraviolet absorption spectrum (in methanol): As shown in FIG. 5

Figure 6:
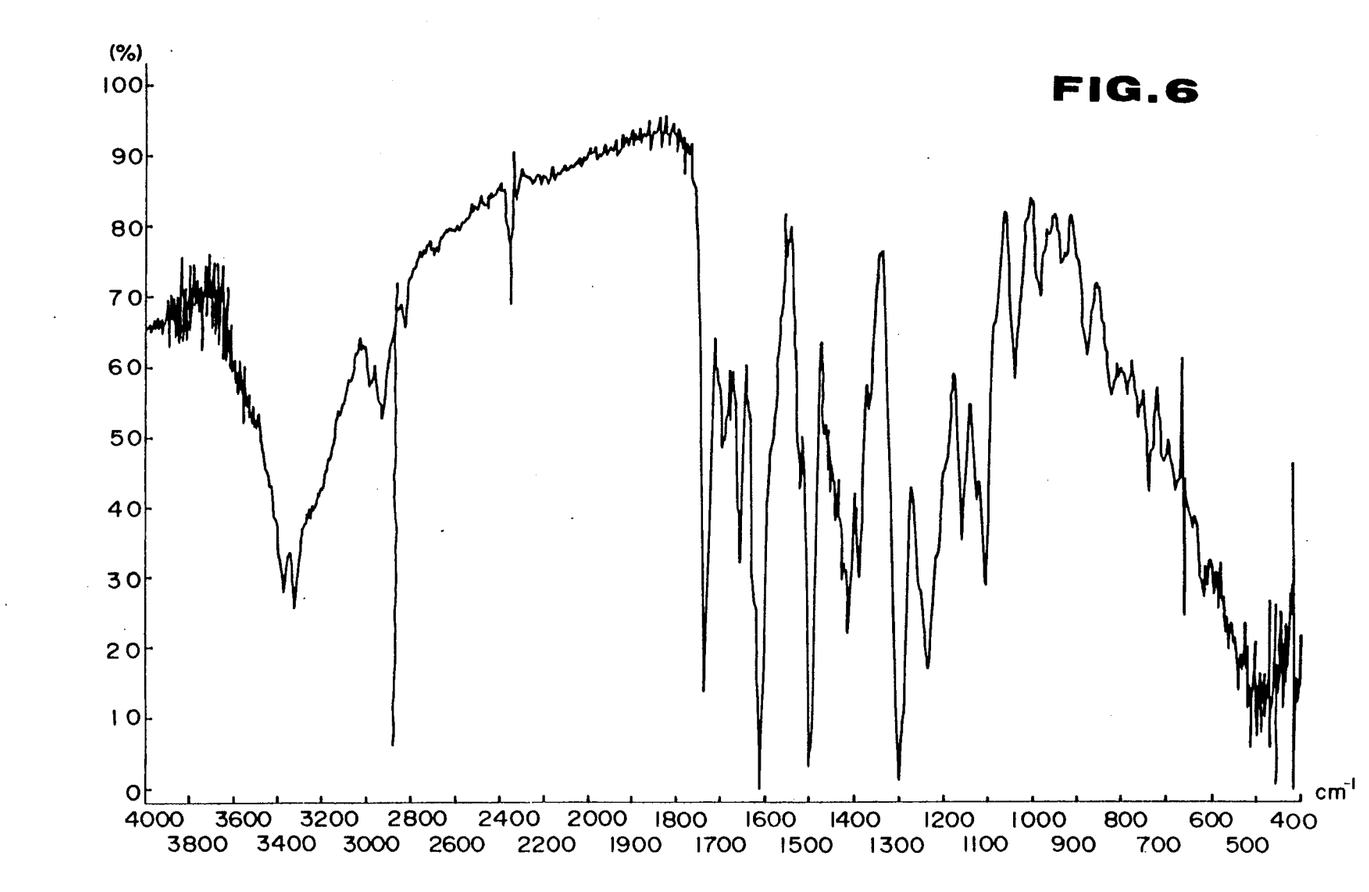
FIG. 6 shows the IR absorption spectrum of DCB-89B2 (KBr tablet).

(6) Infrared absorption spectrum (KBr tablet): As shown in FIG. 6

(7) Specific rotation: $[\alpha]_D^{20} = -57.5°$ (CH$_3$OH solution)

(8) PMR spectrum (in CDCl$_3$, internal standard TMS) 9.52(1H,s), 8.51(1H,s), 6.99(1H,d), 6.84 (1H,s), 4.60(1H,dd), 4.51(1H,dd), 4.15(1H m), 4.13(3H,s), 4.03(1H,dd), 3.95(3H,s), 3.91(3H,s), 3.73(3H,s), 3.59(1H,dd), 1.70 (3H,s)

(9) CMR spectrum (in CDCl$_3$, internal standard TMS) 196.6, 169.5, 160.5, 150.4, 150.1, 144.2, 140.9, 138.7, 137.6, 129.1, 126.0, 123.5, 120.2, 115.6, 112.5, 107.9, 98.0, 71.2, 61.5, 61.2, 56.4, 56.1, 53.4, 42.0, 35.6, 22.0

(10) Solubility: readily soluble in methanol, ethanol, ethyl acetate, acetone, chloroform and dimethylsulfoxide; sparingly soluble in water and n-hexane.

Table 1 shows the Rf values for DC-89A2, DC-89B1 and DC-89B2 obtained by thin layer chromatography [silica gel (HPTLC-plates Art. 15647 manufactured by E. Merck A.G.); developed at room temperature for 10 minutes using acetonitrile:water=9:1 as a developing solvent].

TABLE 1

| Compound | Rf Value |
| --- | --- |
| DC-89A2 | 0.41 |
| DC-89B1 | 0.46 |
| DC-89B2 | 0.42 |

After the development, spots of the DC-89 compounds can be detected by bioassay using *Bacillus subtilis*, by color reaction using hot sulfuric acid, iodine or Ehrlich's reagent, or by UV absorption.

The biological properties of the DC-89 compounds are described below.

(A) Antibacterial activity against various bacteria

The antibacterial activity was determined by the agar dilution method using a medium (pH 7) prepared by dissolving 3 g of Bacto-tryptone (Difco Laboratories), 3 g of meat extract, 1 g of yeast extract, 1 g of glucose and 16 g of agar in 1 liter of water. Table 2 shows the antibacterial activity as minimum inhibitory concentration (MIC).

TABLE 2

| Bacteria Tested | Minimum inhibitory concentration against various bacteria (MIC: µg/ml) | | |
| --- | --- | --- | --- |
|  | DC-89A2 | DC-89B1 | DC-89B2 |
| *Staphylococcus aureus* ATCC 6538P | 0.052 | 0.0008 | 0.0033 |
| *Bacillus subtilis* No. 10707 | 0.0065 | 0.013 | 0.0033 |
| *Klebsiella pneumoniae* ATCC 10031 | 0.42 | 0.026 | 0.10 |
| *Escherichia coli* ATCC 26 | 5.2 | 0.33 | 1.3 |
| *Salmonella typhi* ATCC 9992 | 10.4 | 1.3 | 2.6 |

(B) Acute toxicity

The acute toxicity value (LD$_{50}$) was about 3.83 mg/kg with DC-89A2, about 0.37 mg/kg with DC-89B1 and about 0.28 mg/kg with DC-89B2, when they were intraperitoneally administered to mice.

(C) Anti-tumor activity (1) Therapeutical effect against Sarcoma 180 solid tumor Six ddY male mice each weighing about 20 g were used for each group, and $5 \times 10^6$ Sarcoma 180 solid tumor cells were implanted subcutaneously into the mice at the axilla. Twenty-four hours after the implantation, 0.2 ml of a phosphate buffer saline (hereinafter referred to as PBS) containing the DC-89 compound in the concentration shown in Table 3 was intraperitoneally administered once.

The composition of PBS was 0.8 g/dl NaCl, 0.02 g/dl KCl, 1.15 g/dl Na$_2$HPO$_4$ and 0.02 g/dl KH$_2$PO$_4$ (pH 7.2).

For comparison, 0.2 ml of PBS containing mitomycin C was intraperitoneally administered 24 hours after implantation of the tumor cells.

Ten days after the implantation, T/C [T: average tumor volume (mm$^3$) of the test groups, C: average tumor volume (mm$^3$) of the control group which received an intraperitoneal administration of 0.2 ml of PBS] was determined.

The results are shown in Table 3.

TABLE 3

| Test Compound | Dose (mg/kg) | T/C |
| --- | --- | --- |
| DC-89A2 | 3 | 0.19 |
| DC-89B1 | 0.5 | 0.22 |
| DC-89B2 | 0.25 | 0.28 |
| Mitomycin C | 4 | 0.30 |

(2) Therapeutical effect against lymphocytic leukemia P388

Five male CDF$_1$ mice each weighing about 22 g were used for each group, and $1 \times 10^6$ cells of lymphocytic leukemia P388 tumor cells were implanted intraperitoneally into the mice. Twenty-four hours after the implantation, 0.2 ml of PBS containing the DC-89 compound was intraperitoneally administered once. For comparison, 0.2 ml of PBS containing mitomycin C was intraperitoneally administered 24 hours after implantation of the tumor cells. The increased life span (T/C) [T: mean survival time (days) of the test groups, C: mean survival time (days) of the control group which received an intraperitoneal administration of 0.2 ml of PBS] after the implantation is shown in Table 4.

TABLE 4

| Test Compound | Dose (mg/kg) | Increased Life Span (T/C) |
| --- | --- | --- |
| DC-89A2 | 0.125 | 1.35 |
| DC-89B1 | 0.0156 | 1.35 |
| DC-89B2 | 0.0781 | 1.19 |
| Mitomycin C | 4 | 1.66 |

The processes for producing the DC-89 compounds and DC-89A1 are described below.

The DC-89 compounds can be obtained by culturing in a medium a microorganism belonging to the genus Streptomyces and being capable of producing the DC-89 compounds, allowing the DC-89 compounds to accumulate in the culture and recovering the DC-89 compounds from the culture.

Any microorganism may be used in the present invention so long as it belongs to the genus Streptomyces and is capable of producing the DC-89 compounds. A preferred example is *Streptomyces lydicus* DO-89 strain (FERM BP-988) described in WO 87/06265.

The method for culturing is described below.

For the culturing in the present invention, conventional methods for culturing Actinomycetes are generally used. As the medium, either a synthetic medium or a natural medium can be employed so long as it contains proper amounts of assimilable carbon sources, nitrogen sources and inorganic matters and adequately contains substances for accelerating growth of the microorganism or production of the DC-89 compounds.

As the carbon source, glucose, starch, dextrin, mannose, fructose, sucrose, lactose, xylose, arabinose, mannitol, molasses, etc. can be used either alone or in combination. Furthermore, hydrocarbons, alcohols, organic acids and the like can also be used depending on the assimilability of the strain. As the nitrogen source, ammonium chloride, ammonium sulfate, sodium nitrate, urea, peptone, meat extract, yeast extract, dry yeast, corn steep liquor, soybean meal, Casamino acid, etc. can be used either alone or in combination. If necessary, inorganic salts such as sodium chloride, potassium chloride, potassium bromide, magnesium sulfate, potassium dihydrogenphosphate, dipotassium hydrogenphosphate, ferrous sulfate, calcium chloride, manganese sulfate, zinc sulfate and copper sulfate can also be added to the medium. In addition, substances capable of promoting growth of the strain used or production of the DC-89 compounds, for example, vitamin $B_1$ and biotin, can be appropriately added.

Culturing is usually carried out by liquid culture, and most preferably by submerged culture with stirring. Culturing temperature is 25° to 40° C., preferably 28° to 38° C. It is desirable to maintain the pH of the medium at 4 to 10, preferably 6 to 8 by adding aqueous ammonia, ammonium carbonate solution, etc. during the culturing.

Usually after one to seven days of liquid culture, the desired substance is formed and accumulated in the culture broth and microbial cells.

Culturing is discontinued when the amount of the product in the culture reaches the maximum. Then, the product is isolated and purified from the culture.

Isolation and purification of the DC-89 compounds from the culture are carried out by conventional methods for isolating and purifying microbial metabolites from culture. For example, the culture is separated into culture filtrate and microbial cells by filtration. The cells are extracted with n-propanol, chloroform, acetone, etc., and the extract is combined with the culture filtrate. The mixture is passed through a column packed with a non-ionic porous resin such as Diaion HP-20 (Mitsubishi Kasei Corporation) to adsorb the active component. Then, the adsorbed active component is eluted with methanol, acetone, etc. and the eluate is concentrated. Water (pH 5-6) and ethyl acetate are added to the concentrate, followed by shaking, whereby the active component is transferred into the ethyl acetate layer.

The ethyl acetate layer is concentrated to dryness to give crude powder of the DC-89 compound. The crude powder can be further purified by procedures such as crystallization and chromatography using Sephadex, silica gel, etc.

Alternatively, the DC-89 compounds, as well as DC-89A1, can be produced either by reaction of DC-88A with hydrochloric acid or hydrobromic acid, or by reaction of DC-88A with a compound represented by the general formula:

$$MX_n \qquad (I)$$

wherein M represents lithium, sodium, potassium, calcium, magnesium, aluminum, zinc or copper; X represents chlorine or bromine; and n represents an integer of 1 to 3, in a buffer solution (pH 3-6).

DC-89A1 and DC-89A2 can be produced by allowing DC-88A to react with hydrochloric acid or hydrogen chloride in an inert solvent. As the inert solvent, acetonitrile, methylene chloride, dimethylformamide, ethyl acetate, tetrahydrofuran, acetone, water, etc. may be used singly or as a mixture. Hydrochloric acid or hydrogen chloride is generally used in an amount of 1 to 50 equivalents based on 30 DC-88A. The reaction is generally carried out at −20 to 30° C. and completed in 5 minutes to 2 hours.

DC-89B1 and DC-89B2 can be produced by the same reaction as above, except that hydrobromic acid is used instead of hydrochloric acid.

Furthermore, DC-89A1, DC-89A2, DC-89B1 and DC-89B2 can also be produced by allowing DC-88A to react with the compound [hereinafter referred to as Compound (I)] represented by the general formula:

$$MX_n \qquad (I)$$

wherein M, X and n have the same significances as defined above, in a solvent mixture of an inert solvent and a buffer solution (pH 3-6). As the inert solvent, acetonitrile, dimethylformamide, tetrahydrofuran, acetone, methylene chloride, etc. may be used singly or as a mixture.

Compound (I) is usually used in an amount of 2 to 30 equivalents based on DC-88A. As the buffer solution having a pH value of 3 to 6, 0.02 to 1 M acetate buffer solution, citrate buffer solution, phosphate buffer solution, etc. can be used. The reaction is carried out generally at 0° to 60° C. and completed in one hour to 3 days.

After completion of the reaction in each step, a buffer solution or water is added to the reaction mixture if necessary, followed by extraction with a water-immiscible solvent such as ethyl acetate, chloroform and ether. After washing with water, an aqueous sodium chloride solution, etc., the extract is dried over anhydrous sodium sulfate and the solvent is distilled away. The residue is subjected to silica gel column chromatography, thin layer chromatography, high performance liquid chromatography, recrystallization, etc. for purification.

The DC-89 compounds themselves and compositions comprising effective amounts of them and pharmaceutical vehicles can be used as antibiotics and anti-tumor agents. The pharmaceutical vehicles as used herein include diluents, excipients, disintegrators, binders, lubricants, bases, etc. which are conventionally used.

The DC-89 compounds can be used in various administration forms. When the DC-89 compound is administered in the form of injection, the compound is dissolved in a diluent conventionally used in the art, for example, in ethanol, optionally with a surfactant or a solubilizing agent, and after ethanol is removed by suction if necessary, the solution is mixed with distilled water for injection, physiological saline or distilled water for injection containing glucose, fructose, mannitol, etc. to prepare an injection.

Alternatively, the ethanol solution may be freeze-dried or the compound may be mixed with sodium chloride to prepare a powder preparation for injection, which is dissolved before each application. These injections are administered, for example, intravenously. Intramuscular administration, intraarterial administration, intraperitoneal administration, intrathoracic administration, etc. are also possible.

Preparations for oral administration are prepared by mixing the DC-89 compound with an appropriate excipient, disintegrator, binder, lubricant, etc. and forming the mixture into tablets, granules or powders in a conventional manner.

Dosage may vary depending upon the administration route, the kind of the DC-89 compound, the age and condition of a patient, etc., but an appropriate daily dose to mammals including humans is generally 0.5 to 75 mg of the DC-89 compound/60 kg.

Examples of the present invention are shown below. In the examples, the DC-89 compounds were traced by bioassay using *Bacillus subtilis* No. 10707, or by thin layer chromatography or high performance liquid chromatography using UV absorption of each compound as indication.

EXAMPLE 1

Streptomyces lydicus DO-89 (FERM BP-988) was used as the seed strain. The strain was inoculated into 200 ml of a seed medium [25 g/l soluble starch, 5 g/l glucose, 1 g/l yeast extract, 10 g/l Peptone-A (Kyokuto Pharmaceutical Co., Ltd.) and 1 g/l calcium carbonate; pH 7.2 before sterilization] in a 2-l Erhlenmeyer flask and subjected to shaking culture (200 r.p.m.) at 28° C. for 48 hours.

The resulting seed culture was transferred to a 30-l jar fermenter containing 15 l of a medium having the same composition as the above seed medium in a ratio of 5% (by volume) and cultured with stirring and aeration (rotation: 200 r.p.m., aeration: 15 l/min) at 28° C. for 24 hours. The obtained culture was transferred to a 200-l tank fermenter containing 150 l of a medium having the following composition in a ratio of 10% (by volume) and cultured with stirring and aeration (rotation: 200 r.p.m., aeration: 15 l/min) at 28° C.

Composition of the fermentation medium: 50 g/l maltose, 15 g/l dry yeast, 25 g/l Ebios (Asahi Breweries, Ltd.), 10 g/l KCl, 0.5 g/l $KH_2PO_4$, 0.5 g/l $MgSO_4 \cdot 7H_2O$, 5 g/l calcium carbonate (pH 5.0; adjusted with 6N $H_2SO_4$ prior to sterilization).

Culturing was carried out for 100 hours without controlling the pH of the medium. The cells and the precipitate were separated from the culture by filtration to give 100 l of a filtrate. To the cells and the precipitate was added 50 l of n-propanol, and after thorough mixing, the mixture was filtered to give 45 l of n-propanol extract. The culture filtrate and the n-propanol extract were combined (total volume: 140 l), and the mixture was passed through 5 l of Diaion HP-20 (Mitsubishi Kasei Corporation) to adsorb the active component. After the column was washed with water and then with 70% aqueous methanol solution, elution was carried out with methanol. The methanol-eluted fractions were concentrated and the concentrate was extracted with 10 l of ethyl acetate. The ethyl acetate extract was concentrated, and n-hexane was added to the concentrate to give a crude powder of DC-89A2. The crude powder of DC-89A2 was then recrystallized from methanol to give 1 g of pure DC89A2. The thus obtained DC-89A2 showed the physicochemical properties, antibacterial activity and anti-tumor activity described above.

EXAMPLE 2

Culturing was carried out in a similar manner as in Example 1 except that the fermentation medium having the following composition was used.

Composition of the fermentation medium: 50 g/l maltose, 15 g/l dry yeast, 25 g/l Ebios (Asahi Breweries, Ltd.), 10 g/l KBr, 0.5 g/l $KH_2PO_4$, 0.5 g/l $MgSO_4 \cdot 7H_2O$, 5 g/l calcium carbonate (pH 5.0; adjusted with 6N $H_2SO_4$ prior to sterilization).

After the pH of the resulting culture was adjusted to 4.5 with 12N HCl, the cells and the precipitate were separated from the culture by filtration to give 100 l of a filtrate. To the cells and the precipitate was added 50 l of n-propanol, and after thorough mixing, the mixture was filtered to give 45 l of n-propanol extract. The culture filtrate and the n-propanol extract were combined (total volume: 140 l), and the mixture was passed through 5 l of Diaion HP-20 (Mitsubishi Kasei Corporation) to adsorb the active component. After the column was washed with water and then with 70% aqueous methanol solution, elution was carried out with methanol to give the methanol-eluted fractions containing DC-89B1 and the methanol-eluted fractions containing DC-89B2. The fractions containing DC-89B1 were concentrated and the concentrate was passed through 200 ml of Diaion HP-20SS (Mitsubishi Kasei Corporation), followed by elution with 80% aqueous methanol solution of pH 4.0. The eluted fractions containing DC-89B1 were concentrated and the concentrate was extracted with ethyl acetate. The ethyl acetate extract was concentrated, and n-hexane was added to the concentrate to give 0.5 g of pure DC-89B1. The thus obtained DC-89B1 showed the physicochemical properties, antibacterial activity and anti-tumor activity described above.

The methanol-eluted fractions containing DC-89B2 were concentrated and the concentrate was passed through 500 ml of Diaion HP-20SS (Mitsubishi Kasei Corporation), followed by elution with 85% aqueous methanol solution of pH 4.0. The eluted fractions containing DC-89B2 were concentrated and the concentrate was extracted with ethyl acetate. The ethyl acetate extract was concentrated, and n-hexane was added to the concentrate to give a crude powder of DC-89B2. The crude powder of DC-89B2 was recrystallized from methanol to give 1.5 g of pure DC-89B2. The thus obtained DC-89B2 showed the physicochemical properties, antibacterial activity and anti-tumor activity described above.

EXAMPLE 3

DC-88A (30 mg) was dissolved in 2 ml of acetonitrile and 2 ml of 0.1 M citrate buffer (pH 5), and 44 mg of potassium chloride was added to the solution, followed by stirring at room temperature for 7 hours and 40 minutes. The reaction mixture was subjected to high performance liquid chromatography (column: Nucleosil $C_{18}\phi 20$ mm × 250 mm, eluted with 50% acetonitrile-water, 10 ml/min) to give 5.3 mg (yield 16.5%) of DC-89A1 and 24.2 mg (yield 75.3%) of DC-89A2.

What is claimed is:

1. Novel DC-89 compounds represented by the general formula:

wherein X represents a single bond or —CH$_2$—; and when X represents a single bond, Y represents —CH$_2$Br and when X represents —CH$_2$—, Y represents Br.

* * * * *